US012653416B2

(12) United States Patent
Govari et al.

(10) Patent No.: US 12,653,416 B2
(45) Date of Patent: Jun. 16, 2026

(54) WIRELESS MEDICAL LOCATION TRACKING

(71) Applicant: Biosense Webster (Israel) Ltd., Yokneam (IL)

(72) Inventors: Assaf Govari, Haifa (IL); Andres Claudio Altmann, Haifa (IL); Vadim Gliner, Haifa (IL); Alon Boumendil, Givat Nili (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 250 days.

(21) Appl. No.: 18/206,284

(22) Filed: Jun. 6, 2023

(65) Prior Publication Data

US 2024/0407665 A1    Dec. 12, 2024

(51) Int. Cl.
*A61B 5/06*        (2006.01)
*A61B 34/20*       (2016.01)

(52) U.S. Cl.
CPC .............. *A61B 5/062* (2013.01); *A61B 34/20* (2016.02)

(58) Field of Classification Search
CPC ......... A61B 5/062; A61B 5/282; A61B 34/20; A61B 5/283; A61B 5/308; A61B 2560/045; A61B 5/002; A61B 5/6823; A61B 5/6852; A61B 5/6869; A61B 5/0004
See application file for complete search history.

(56) References Cited

U.S. PATENT DOCUMENTS

| | | |
|---|---|---|
| 5,391,199 A | 2/1995 | Ben-Haim |
| 5,443,489 A | 8/1995 | Ben-Haim |
| 5,558,091 A | 9/1996 | Acker et al. |
| 6,172,499 B1 | 1/2001 | Ashe |
| 6,239,724 B1 | 5/2001 | Doron et al. |
| 6,332,089 B1 | 12/2001 | Acker et al. |
| 6,484,118 B1 | 11/2002 | Govari |
| 6,618,612 B1 | 9/2003 | Acker et al. |
| 6,690,963 B2 | 2/2004 | Ben-Haim et al. |
| 6,788,967 B2 | 9/2004 | Ben-Haim et al. |
| 6,892,091 B1 | 5/2005 | Ben-Haim et al. |
| 7,536,218 B2 | 5/2009 | Govari et al. |
| 7,756,576 B2 | 7/2010 | Levin |

(Continued)

OTHER PUBLICATIONS

European Search Report for corresponding EPA No. 24180100.0 dated Sep. 23, 2024.

*Primary Examiner* — Christopher Koharski
*Assistant Examiner* — Steven Maldonado
(74) *Attorney, Agent, or Firm* — Calderon Safran & Wright P.C.; Etan S. Chatlynne

(57)        ABSTRACT

In one embodiment, a dongle apparatus configured to augment a patient interface unit (PIU) retrofitted with the dongle apparatus, and including a connector configured to be physically connected to an interface of the PIU, at least three load circuits configured to receive at least three corresponding alternating current (AC) signals from the PIU via the connector and mimic a load of at least three corresponding magnetic field generator coils of a location pad, sampling circuitry configured to sample a current amplitude and a phase of the at least three AC signals in the at least three load circuits, and wireless communication circuitry configured to wirelessly send data about the current amplitude and the phase of the at least three AC signals to a driver of the location pad. Other embodiments are described herein.

7 Claims, 4 Drawing Sheets

(56)  References Cited

U.S. PATENT DOCUMENTS

| | | |
|---|---|---|
| 7,848,787 B2 | 12/2010 | Osadchy |
| 7,869,865 B2 | 1/2011 | Govari et al. |
| 8,456,182 B2 | 6/2013 | Bar-Tal et al. |
| 9,636,031 B2 | 5/2017 | Cox |
| 11,273,288 B2 | 3/2022 | McMichael et al. |
| 2003/0120150 A1 | 6/2003 | Govari |
| 2013/0015848 A1* | 1/2013 | Govari ................... A61B 34/20 |
| | | 324/228 |
| 2014/0275890 A1 | 9/2014 | Meehan et al. |
| 2018/0132945 A1* | 5/2018 | Fazzi ..................... A61B 34/20 |
| 2019/0159843 A1 | 5/2019 | Demri et al. |
| 2021/0077201 A1 | 3/2021 | Cox et al. |

* cited by examiner

WIRELESS MEDICAL LOCATION TRACKING

FIELD OF THE DISCLOSURE

The present disclosure relates to medical devices, and in particular, but not exclusively, to wireless location tracking.

BACKGROUND

A wide range of medical procedures involve placing probes, such as catheters, within a patient's body. One medical procedure in which these types of probes or catheters have proved extremely useful is in the treatment of cardiac arrhythmias. Cardiac arrhythmias and atrial fibrillation in particular, persist as common and dangerous medical ailments, especially in the aging population.

Diagnosis and treatment of cardiac arrhythmias include mapping the electrical properties of heart tissue, especially the endocardium and the heart volume, and selectively ablating cardiac tissue by application of energy. Catheters are inserted into the heart chamber and optionally around the heart chamber during such procedures. In most procedures, multiple catheters are inserted into the patient. Catheters may include mapping, ablation, temperature sensing and image sensing catheters. Some catheters are dedicated for placement in specific parts of the anatomy, e.g., coronary sinus, esophagus, atrium, ventricle. The catheters have multiple electrical channels, some more than others depending on the number of sensors and electrodes included in each catheter. The number and type of catheters depends on the procedure and on the physician preferred workflow.

BRIEF DESCRIPTION OF THE DRAWINGS

The present disclosure will be understood from the following detailed description, taken in conjunction with the drawings in which.

DESCRIPTION OF EXAMPLES

Overview

Figure 1:
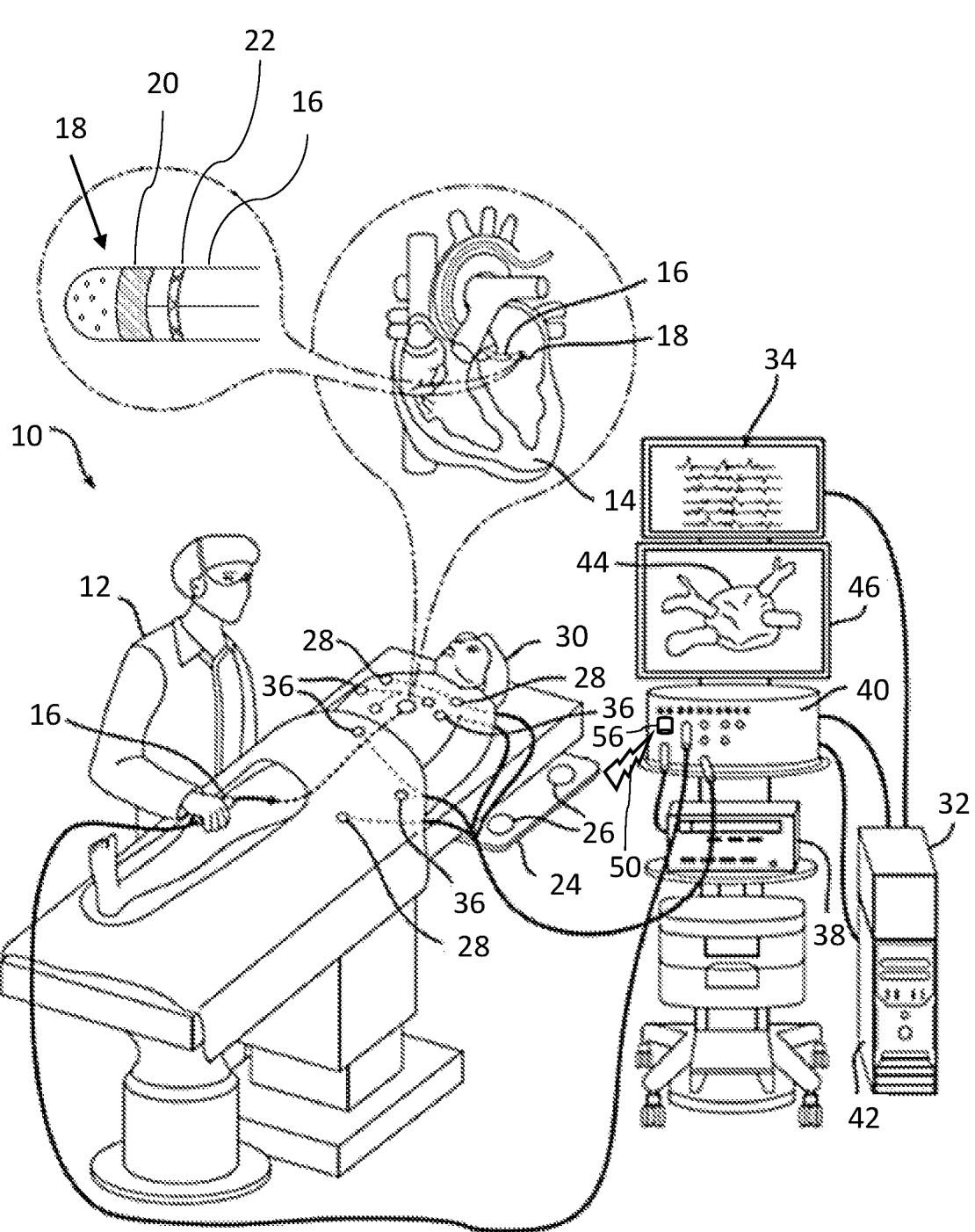
FIG. 1 is a pictorial view of a catheter-based electrophysiology mapping and ablation system constructed and operative in accordance with an exemplary mode of the present disclosure.

Location tracking of catheters and similar medical devices may be performed using various tracking methods including magnetic-based tracking. In magnetic based tracking, alternating current (AC) signals are applied to magnetic field generator coils in a location pad which is generally positioned below a part of a patient and the various magnetic fields are sensed using magnetic sensor(s) in a catheter, for example. The catheter and the location pad are typically physically connected to a patient interface unit (PIU). The PIU provides an interface for communicating with each of a plurality of devices that are operated during a medical procedure for diagnosing and/or treating cardiac arrhythmias. The PIU generates the signals for driving the magnetic field generator coils in the location pad. The PIU may additionally sample output from the catheters, generate signals to be transmitted to one or more devices, perform some signal processing tasks, and compute the position of the catheter or send data to another processing device to compute the position of the catheter. The position of the catheter is computed based on comparing the current and phase of the signals in the magnetic field generator coils of the location pad with corresponding signals sensed by the magnetic sensor(s) in the catheter. The above tracking method provides a safe and accurate method of tracking the catheter.

One drawback of the above system is that the cable connecting the PIU with the location pad is often an obstacle in the electrophysiological procedure room. The cable may be a tripping hazard leading to accidents. In some cases, the cable may become disconnected from the PIU or the location pad leading to malfunctioning of the system.

On solution to the above drawback is to provide a wireless connection between the PIU and the location pad and transmit the signals wirelessly from the PIU to the location pad. However, as the current amplitude through the magnetic field generator coils may change over time due to temperature changes, which in turn leads to induction and resistance changes, the PIU may be unaware of the current in the coils and therefore incapable of computing the position of the catheter. Additionally, in many cases replacing the PIU and location pad with a wireless system is impractical due to the great number of PIU devices already installed in medical centers that will have to be disposed of, and replaced, at great cost.

Therefore, exemplary modes of the present disclosure provide a PIU which is connected to a location pad wirelessly, while allowing the PIU or a processing device connected to the PIU to compute the position of one or more catheters connected to the PIU.

In some exemplary modes, the PIU is retrofitted with a dongle to augment the PIU. The location pad may include a location pad driver to augment the location pad. In this manner, a legacy PIU and location pad may be used to communicate with each other wirelessly. In some exemplary modes, the existing hardware and software of the legacy PIU does not need to be changed at all. In fact, the PIU may operate in the same manner as it did when the PIU and location pad were connected directly by a cable. Optionally, the location pad is also retrofitted with the driver.

The dongle physically connects to one of the ports of the PIU and includes three or more load circuits (corresponding to the number of magnetic field generator coils in the location pad) which are driven by at least three corresponding AC signals (at different frequencies) generated by the PIU and mimic a load of the corresponding magnetic field generator coils of the location pad. The dongle samples each AC signal to determine its current amplitude and phase and sends data about the determined current amplitude and the phase of each AC signal to the location pad.

The location pad driver physically connects to the location pad, e.g., is integral to the location pad and wirelessly receives from the dongle the data about the current amplitude and the phase of each AC signal generated in the dongle. A signal generator of the location pad driver generates three or more (e.g., nine) AC signals (corresponding to the number of magnetic field generator coils in the location pad) based on the data received (i.e., based on the current amplitude and phase of the signals generated in the load circuits of the dongle connected to the PIU). The AC signals are generated at constant current equal to the current amplitudes received in the data from the PIU (dongle)

(irrespective of the temperature, impedance, or resistance of the location pad coils). The AC signals are maintained at the constant current by monitoring the current amplitudes of the AC signals in the location pad circuits and adjusting the AC signals accordingly. The AC signals drive the location pad magnetic field generator coils to generate magnetic fields in a region around the location pad.

The PIU computes positions of the catheter(s) connected to the PIU based on the signals received from the catheter(s) and the current amplitude and phase of the AC signals generated in the PIU as sampled in the dongle. As the amplitude and phase of the AC signals in the magnetic coils of the location pad are maintained at the same amplitude and phase as the AC signals in the dongle, the PIU does not need to know what it is happening with the coils in the location pad as the current amplitude and phase of the AC signals generated in the location pad driver should be the same as the signals generated in the PIU.

In some exemplary modes, the dongle and the location pad driver may include clocks which are synchronized intermittently. Optionally, the phase of the signals in the dongle and the location pad driver may need further synchronization due to timing differences in the clocks and delays related to communication and signal processing.

In some exemplary modes, the PIU may incorporate elements of the dongle and/or the location pad may incorporate elements of the location pad driver to build wireless functionality into the PIU and location pad without using dongles or additional drivers.

In some exemplary modes, the location pad generates AC signals to drive the magnetic coils, and the location pad samples the current amplitude and the phase of the signals in the circuits of the magnetic field generator coils of the location pads and wirelessly sends these measurements back to the PIU. The PIU may then compute the positions of the catheter(s) based on the actual current amplitude and phase of the signals in the magnetic field generator coils as well as based on the output of position sensing coils in the catheter.

System Description

Reference is made to FIG. 1, which is a pictorial view of a catheter-based electrophysiology mapping and ablation system 10 constructed and operative in accordance with an exemplary mode of the present disclosure. System 10 includes multiple catheters, which are percutaneously inserted by a physician 12 through the patient's vascular system into a chamber or vascular structure of a heart 14. Typically, a delivery sheath catheter is inserted into the left or right atrium near a desired location in heart 14. Thereafter, one or more catheters may be inserted into the delivery sheath catheter so as to arrive at the desired location in heart 14. The plurality of catheters may include catheters dedicated for sensing Intracardiac Electrogram (IEGM) signals, catheters dedicated for ablating and/or catheters dedicated for both sensing and ablating. An example catheter 16 that is configured for sensing IEGMs and performing ablation is illustrated herein. Physician 12 may place a distal tip 18 of catheter 16 in contact with the heart wall for sensing a target site in heart 14. For ablation, physician 12 may similarly place the distal tip 18 of the catheter 16 in contact with a target site for ablating tissue.

Catheter 16 is an exemplary catheter that includes one or more electrodes 20 optionally distributed over the distal tip 18 and configured to sense the IEGM signals. Catheter 16 may additionally include a position sensor 22 embedded in or near distal tip 18 for tracking position and orientation of distal tip 18. Position sensor 22 may be a magnetic based position sensor including three magnetic coils for sensing three-dimensional (3D) position and orientation (including roll).

Magnetic based position sensor 22 may be operated together with a location pad 24 including a plurality of magnetic field generator coils 26 configured to generate magnetic fields in a predefined working volume. Real time position of distal tip 18 of catheter 16 may be tracked based on magnetic fields generated with location pad 24 and sensed by magnetic based position sensor 22. Details of the magnetic based position sensing technology are described in U.S. Pat. Nos. 5,5391,199; 5,443,489; 5,558,091; 6,172,499; 6,239,724; 6,332,089; 6,484,118; 6,618,612; 6,690,963; 6,788,967; 6,892,091.

System 10 may include one or more electrode (body surface) patches 28 positioned for skin contact on patient 30 to establish location reference for location pad 24 as well as impedance-based tracking of electrode(s) 20. For impedance-based tracking, electrical current is directed to electrode(s) 20 and sensed at electrode body surface patches 28 so that the location of each electrode can be triangulated (or otherwise computed) via the electrode patches 28. Details of the impedance-based location tracking technology are described in U.S. Pat. Nos. 7,536,218; 7,756,576; 7,848, 787; 7,869,865; and 8,456,182.

A recorder 32 records and displays electrograms 34 captured with body surface ECG electrodes 36 and intracardiac electrograms (IEGM) captured with electrode(s) 20 of catheter 14. Recorder 32 may include pacing capability for pacing the heart rhythm and/or may be electrically connected to a standalone pacer.

System 10 may include an ablation energy generator 38 that is adapted to conduct ablative energy to the electrode(s) 20 at the distal tip 18 of the catheter 16 configured for ablating. Energy produced by ablation energy generator 38 may include, but is not limited to, radiofrequency (RF) energy or pulsed-field ablation (PFA) energy, including monopolar or bipolar high-voltage DC pulses as may be used to effect irreversible electroporation (IRE), or combinations thereof.

Patient interface unit (PIU) 40 is an interface configured to establish electrical communication between catheters, other electrophysiological equipment, power supply and a workstation 42 for controlling operation of system 10. Electrophysiological equipment of system 10 may include for example, multiple catheters, location pad 24, body surface ECG electrodes 36, electrode patches 28, ablation energy generator 38, and recorder 32. Optionally and preferably, PIU 40 additionally includes processing capability for implementing real-time computations of location of the catheters and for performing ECG calculations. FIG. 1 shows that the PIU 40 and the location pad 24 are connected via a wireless link 50 described in more detail below with reference to FIGS. 2-4. System 10 includes a dongle 56 which is plugged into one of the ports of the PIU 40 and provides wireless functionality between the PIU 40 and the location pad 24 as described in more detail with reference to FIGS. 2 and 3.

Workstation 42 includes memory, processor unit with memory or storage with appropriate operating software stored therein, and user interface capability. Workstation 42 may provide multiple functions, optionally including (1) modeling the endocardial anatomy in three-dimensions (3D) and rendering a model or anatomical map 44 for display on a display device 46, (2) displaying on a display device 46 activation sequences (or other data) compiled from recorded electrograms 34 in representative visual indicia or imagery superimposed on the rendered anatomical map 44, (3) displaying real-time location and orientation of multiple catheters within the heart chamber, and (4) displaying on display device 46 sites of interest such as places where ablation energy has been applied. One commercial product embodying elements of the system 10 is available as the CARTO™3 System, available from Biosense Webster, Inc., 31A Technology Drive, Irvine, CA 92618.

Figure 2:
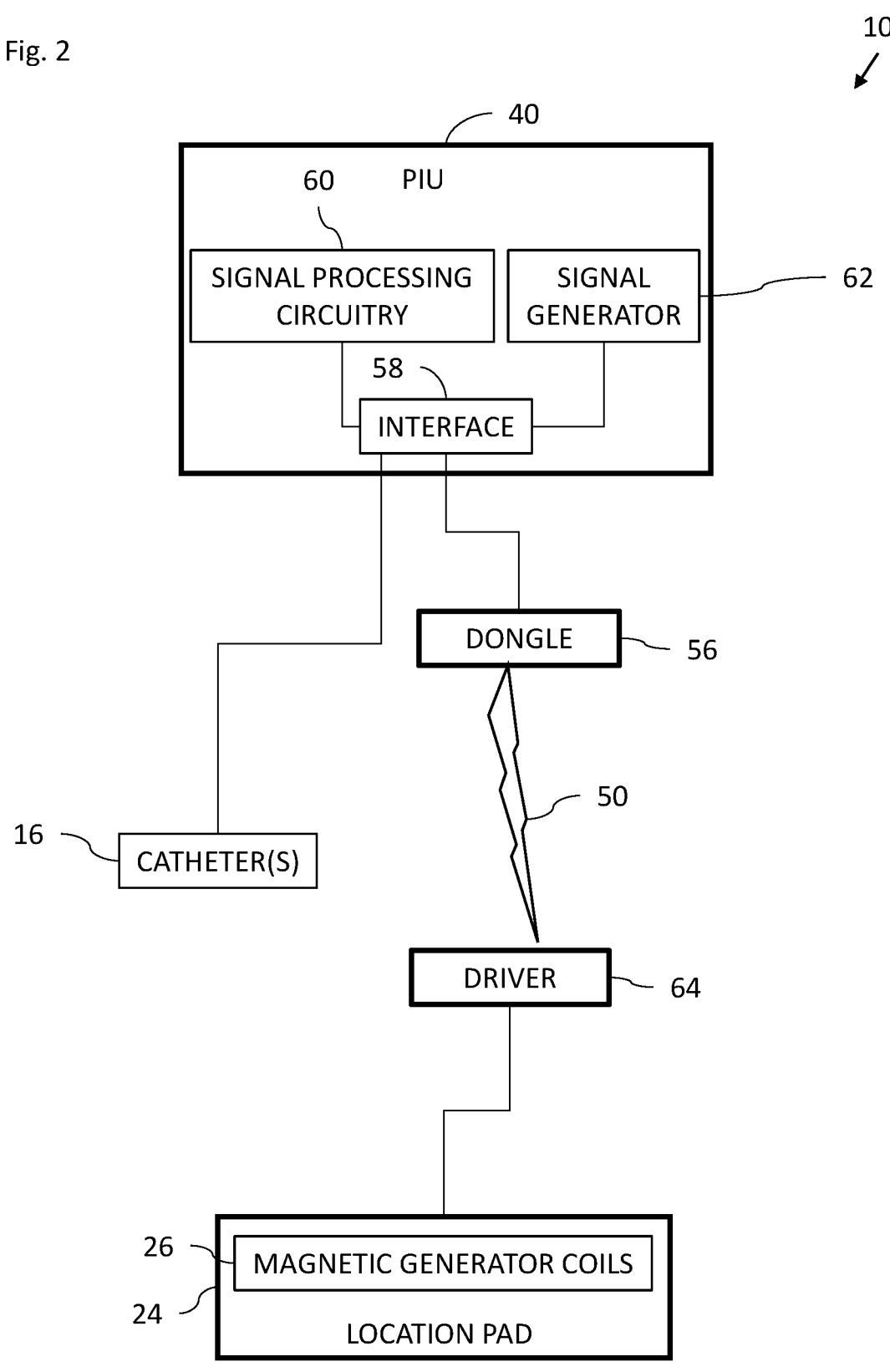
FIG. 2 is a block diagram view of a PIU and a location pad in the system of FIG. 1.

Reference is now made to FIG. 2, which is a block diagram view of a PIU 40 and a location pad 24 in the system 10 of FIG. 1.

The dongle 56 is configured to augment the PIU 40. PIU 40 is retrofitted with the dongle 56. The dongle 56 is described in more detail with reference to FIG. 3. The PIU 40 includes an interface 58 with ports configured to be connected to catheter(s) 16, body surface ECG electrodes 36, electrode body surface patches 28, and the dongle 56. The dongle 56 wirelessly connects (via wireless link 50) the PIU 40 to the location pad 24 as described in more detail with reference to FIG. 3. The PIU 40 also includes: signal processing circuitry 60 configured to process signals received from the catheter(s) 16, for example IEGMs, or to compute a position of the catheter(s) 16; and a signal generator 62 configured to generate signals used by the dongle 56 described in more detail with reference to FIG. 3. Wireless link 50 may be configured for one-way communication from PIU 40 to the location pad 24 or may be configured for two-way communication between PIU 40 and location pad 24.

The location pad 24 including at least three (and typically nine) magnetic field generator coils 26 disposed in the location pad 24 at different orientations to generate at least three (and typically nine) corresponding alternating magnetic fields in a region around the location pad 24 responsively to corresponding AC signals being applied to the coils 26, respectively. The location pad 24 may include three sets of three magnetic field generator coils 26 (i.e., nine magnetic field generator coils 26). The location pad 24 also includes a driver 64 configured to augment the location pad 24 and to be (reversibly) connected to the location pad 24. Alternatively, driver 64 is permanently tethered to location pad 24 and/or integral to location pad 24. Optionally, location pad 24 is retrofitted with driver 64. Driver 64 may include controlling and/or processing capability, e.g., a controller associated with processing capability for controlling operation of driver 64.

Figure 3:
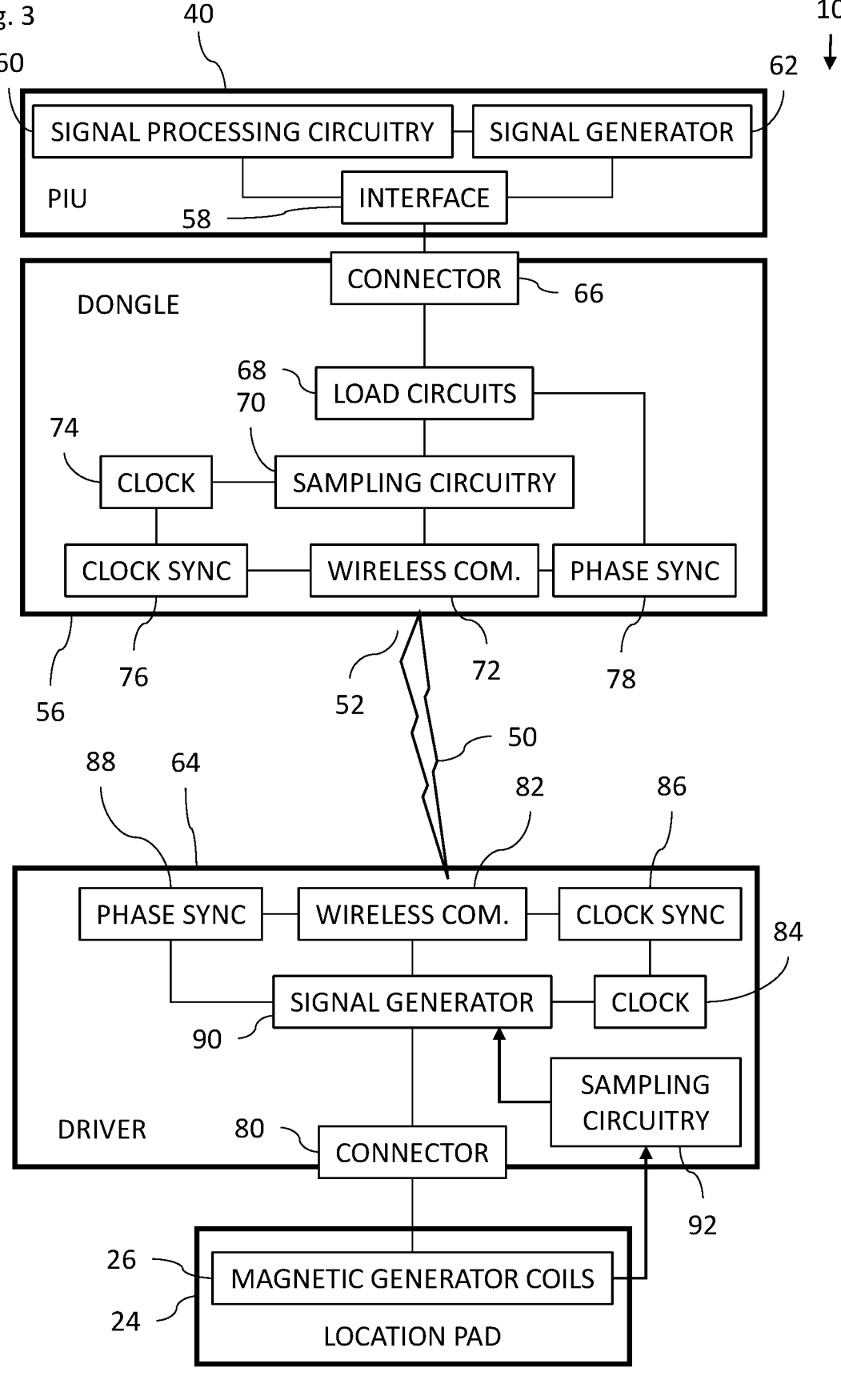
FIG. 3 is a detailed block diagram view of the PIU and location pad of FIG. 2.

Reference is now made to FIG. 3, which is a detailed block diagram view of the PIU 40 and the location pad 24 of FIG. 2.

The dongle 56 includes a connector 66, load circuits 68, sampling circuitry 70, wireless communication circuitry 72, a clock 74, clock synchronization circuitry 76, and phase synchronization circuitry 78.

The connector 66 is configured to be (reversibly) physically connected to a port of the interface 58 of the PIU 40 (e.g., by plugging in the connector 66 into a port (not shown) of the interface 58). The signal generator 62 is configured to generate AC signals, one signal for each of the load circuits 68 in the dongle 56. The AC signals generally have different frequencies for different load circuits 68. The dongle 56 may include any suitable number of load circuits 68. In some examples, the dongle 56 includes nine load circuits 68 corresponding to the number of magnetic field generator coils 26 in the location pad 24. The load circuits 68 are configured to receive the corresponding AC signals (generated by the signal generator 62 of the PIU 40) from the PIU 40 via the connector 66. The load circuits 68 are configured to mimic a load of the corresponding magnetic field generator coils 26 of the location pad 24. Each load circuit 68 may include a circuit with a resistor (e.g., a diamond resister) to provide a load mimicking the coils of the location pad 24. As the resistor is stable and stays cool, the current across the resister does not generally change over time and therefore the currents in the load circuits 68 are generally stable.

The sampling circuitry 70 is configured to intermittently sample a current amplitude and a phase of each of the AC signals in the load circuits 68. The sampling circuitry 70 may include differential amplifiers to sample the AC signals and analogue to digital converters to digitize the values of current amplitude and phase. The wireless communication circuitry 72 is configured to wirelessly send characterizing the AC signals (e.g., data about the sampled current amplitude and the phase of the AC signals in the load circuits 68) to the location pad driver 64.

The clock 74 is configured to maintain a clock value and run at a clock frequency. The clock 74 may be synchronized with a clock in the PIU 40. The clock synchronization circuitry 76 is configured to synchronize a remote clock of the driver 64 with the clock value and/or the clock frequency as maintained by the clock 74 as described in more detail below with reference to the driver 64. The clock synchronization circuitry 76 may use any suitable clock synchronization method. The clock value may be used by the sampling circuitry 70 to sample the phase of the signals.

As previously mentioned, the phase of signals generated in the driver 64 (described in more detail below) may not be synchronized with the phase of the signals in the load circuits 68. Therefore, the phase synchronization circuitry 78 is configured to synchronize the phase of the signals generated in the magnetic field generator coils 26 by the driver 64 with the phase of the AC signals in the load circuits 68. In other words, the phase of the signal in magnetic field generator coil A is synchronized with the phase of the signal in load circuit A, and the phase of the signal in magnetic field generator coil B is synchronized with the phase of the signal in load circuit B, and so on. Phase synchronization is described in more detail below with reference to the driver 64.

The driver 64 includes a connector 80, wireless communication circuitry 82, a clock 84, clock synchronization circuitry 86, phase synchronization circuitry 88, and a signal generator 90.

The connector 80 may optionally be configured to be (reversibly) physically connected to the location pad 24. The wireless communication circuitry 82 is configured to wirelessly share data, e.g., data related to the current amplitude and the phase of the AC signals (that were generated by the dongle 56 and/or are to be generated by the signal generator 90) with the dongle 56. In particular, the wireless communication circuitry 82 is configured to wirelessly receive from the dongle 56 data about the current amplitude and the phase of each of the AC signals in the load circuits 68 and generated by the signal generator 62 of the PIU 40. The signal generator 90 is configured to generate AC signals having corresponding different signal frequencies responsively to the wirelessly received data (received from the dongle 56) related to the current amplitude and phase of the AC signals in the load circuits 68 and generated by the signal generator 62 of the PIU 40. The signal generator 90 is configured to provide, via the connector 80, the AC signals generated by the signal generator 90 to the respective magnetic field generator coils 26 disposed in the location pad 24 in order to generate corresponding alternating magnetic fields in the region around the location pad. In other words, the signal generator 90 generates AC signal A for magnetic field generator coil A, and AC signal B for magnetic field generator coil B, and so on.

The signal generator 90 is configured to maintain the AC signals at the current amplitude of the corresponding AC signals in the load circuits 68. In other words, the current amplitude of the signal in magnetic field generator coil A is maintained at the current amplitude of the signal in load circuit A, and the current amplitude of the signal in magnetic field generator coil B is maintained at the current amplitude of the signal in load circuit B, and so on. Similarly, the same phase is maintained. The location pad driver 64 may include sampling circuitry 92 configured to sample a current amplitude of the AC signals in the circuits of the magnetic field generator coils 26 and provide the sampled values to the signal generator 90. The signal generator 90 is configured to adjust the current amplitudes of the AC signals based on the sampled values in order to maintain the AC signals at the amplitude of the AC signals in the load circuits 68.

The clock 84 is configured to maintain a clock value and run at a clock frequency. The clock 84 may be used by the signal generator 90 to generate signals at the correct frequency and phase. The clock synchronization circuitry 86 is configured to synchronize the clock value and/or the clock frequency of the clock 84 with the remote clock 74 disposed in the dongle 56 connected to the PIU 40. The clock synchronization circuitry 86 may implement clock synchronization by sending Gong, or similar messages intermittently, e.g., every millisecond, to the clock synchronization circuitry 76 of the dongle 56.

Due to electronic delay etc., there may be phase differences between the signals generated by the signal generator 90 and the signals in the load circuits 68. Therefore, in some exemplary modes the phase of the signals generated by the signal generator 90 may be adjusted. The phase synchronization circuitry 88 is configured to synchronize the phase of the AC signals generated by the signal generator 90 with the phase of the corresponding AC signals in the load circuits 68 of the dongle 56. The phase synchronization circuitry 88 samples the signals generated by the signal generator 90 and sends the samples of the signals to the phase synchronization circuitry 78 of the dongle 56 via the wireless link 50. The phase synchronization circuitry 78 is configured to multiply each of the received samples with the corresponding signal from the load circuits 68 to determine the phase difference between the multiplied signals. When the product of the multiplication is equal to zero the two signals multiplied together are in phase. The phase synchronization circuitry 78 sends the phase difference for each of the signals to the phase synchronization circuitry 88 via the wireless link 50. The phase synchronization circuitry 88 then adjusts the phase of the signals generated by the signal generator 90.

In practice, some or all of the function of the clock synchronization circuitry and phase synchronization circuitry may be combined in a single physical component or, alternatively, implemented using multiple physical components. These physical components may comprise hard-wired or programmable devices, or a combination of the two. In some examples, at least some of the functions of the clock synchronization circuitry and phase synchronization circuitry processing circuitry may be carried out by a programmable processor under the control of suitable software. This software may be downloaded to a device in electronic form, over a network, for example. Alternatively, or additionally, the software may be stored in tangible, non-transitory computer-readable storage media, such as optical, magnetic, or electronic memory.

Figure 4:
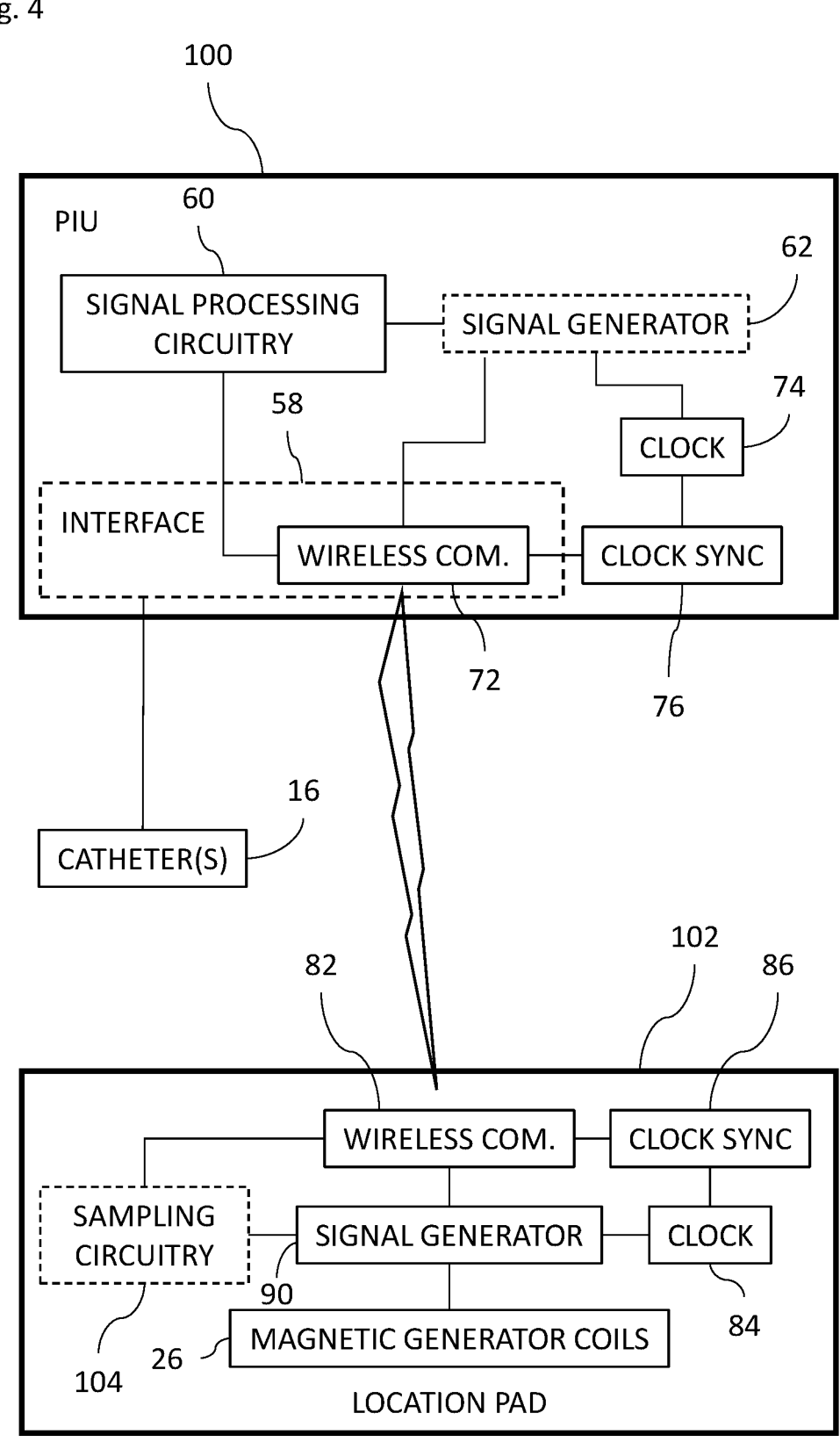
FIG. 4 is a block diagram view of a PIU and a location pad with built-in wireless communication.

Reference is now made to FIG. 4, which is a block diagram view of a PIU 100 and a location pad 102 with built-in wireless communication.

In some exemplary modes, the PIU 100 may be implemented based on combining the functionality of the dongle 56 into the PIU 40 of FIG. 3. In some exemplary modes, the location pad 102 may be implemented based on combining the functionality of the driver 64 into the location pad 24 of FIG. 3.

In other exemplary modes, the PIU 100 may include signal processing circuitry 60, the interface 58 which includes the wireless communication circuitry 72, and optionally the signal generator 62, the clock 74, and the clock synchronization circuitry 76. The interface 58 is configured to be connected to the catheter(s) 16 and wirelessly connected to the location pad 102 via the wireless communication circuitry 72. The wireless communication circuitry 72 is built-in (i.e., the wireless communication circuitry 72 is not part of a dongle or similar pluggable device) to the PIU 100 and is configured to wirelessly communicate with the location pad 102. The signal processing circuitry 60 is configured to process signals received from the catheter(s) 16.

In the other exemplary modes, the location pad 102 may include wireless communication circuitry 82, signal generator 90, magnetic field generator coils 26, sampling circuitry 104, and optionally clock 84, and clock synchronization circuitry. The wireless communication circuitry 82 is built-in (i.e., the wireless communication circuitry 82 is not part of a dongle or similar pluggable device) to the location pad 102.

The signal generator 90 is configured to generate (at least three, e.g., nine) AC signals having (at least three, e.g., nine) corresponding different signal frequencies. The magnetic field generator coils 26 are configured to generate (at least three, e.g., nine) corresponding alternating magnetic fields in a region around the location pad 102 responsively to the AC signals being applied to the magnetic field generator coils 26, respectively, by the signal generator 90.

The controller and/or sampling circuitry 104 is configured to sample the current amplitude and phase of each of the AC signals applied to a corresponding one of the magnetic field generator coils 26. The wireless communication circuitry 82 is configured to wirelessly share data (e.g., send data) about the sampled current amplitude and the phase of the AC signals applied to the magnetic field generator coils 26 with (e.g., to) the PIU 100. The PIU 100 may then process the signals received from the magnetic sensor(s) of the catheter(s) 16 and the data received from the location pad 102 (which indicates the amplitude and phase of the signals in the magnetic field generator coils 26) to compute the positions of the catheter(s) 16.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g., "about 90%" may refer to the range of values from 72% to 108%.

EXAMPLES

Example 1: A dongle apparatus, configured to augment a patient interface unit (PIU) retrofitted with the dongle apparatus, and comprising: a connector configured to be physically connected to an interface of the PIU; at least three load circuits configured to receive at least three corresponding alternating current (AC) signals from the PIU via the connector and mimic a load of at least three corresponding magnetic field generator coils of a location pad; sampling circuitry configured to sample a current amplitude and a phase of the at least three AC signals in the at least three load circuits; and wireless communication circuitry configured to wirelessly send data about the current amplitude and the phase of the at least three AC signals to a driver of the location pad.

Example 2: The apparatus according to example 1, further comprising: a clock configured to maintain a clock value and run at a clock frequency; and clock synchronization circuitry configured to synchronize a remote clock of a driver, which is configured to be connected to the location pad, with at least one of the clock value or the clock frequency.

Example 3: The apparatus according to any one of examples 1 and 2, further comprising phase synchronization circuitry configured to synchronize a phase of signals generated in the at least three corresponding magnetic field generator coils with the phase of the at least three AC signals in the at least three load circuits.

Example 4: A location pad apparatus, comprising: a driver comprising: a signal generator configured to generate at least three alternating current (AC) signals having at least three corresponding different signal frequencies; and wireless communication circuitry configured to wirelessly share data about a current amplitude and a phase of the at least three AC signals with a patient interface unit (PIU); and at least three magnetic field generator coils disposed at different orientations to generate at least three corresponding alternating magnetic fields in a region around the location pad responsively to the at least three AC signals being applied to the at least three magnetic field generator coils, respectively.

Example 5: The apparatus according to example 4, further comprising sampling circuitry configured to sample the current amplitude and phase of the at least three AC signals applied to the at least three magnetic field generator coils, wherein the wireless communication circuitry is configured to wirelessly send the data about the current amplitude and the phase to the PIU.

Example 6: The apparatus according to any one of examples 4 and 5 or example, wherein: the wireless communication circuitry is configured to wirelessly receive the data about the current amplitude and phase from the PIU or the dongle; and the signal generator is configured to generate the at least three AC signals responsively to the wirelessly received data about the current amplitude and phase.

Example 7: The apparatus according to example 6, wherein the signal generator is configured to maintain the at least three AC signals at the current amplitude.

Example 8: The apparatus according to example 7, further comprising sampling circuitry configured to sample current amplitudes of the at least three AC signals in circuits of the magnetic field generator coils and provide the sampled current amplitudes to the signal generator, which is configured to adjust the current amplitudes of the at least AC signals based on the sampled current amplitudes in order to maintain the at least three AC signals at the amplitude of the AC signals in the load circuits.

Example 9: The apparatus according to any one of examples 4-8, wherein the driver also includes: a clock configured to maintain a clock value and run at a clock frequency; and clock synchronization circuitry configured to synchronize at least one of the clock value or the clock frequency with a remote clock disposed in the dongle.

Example 10: The apparatus according to any one of examples 4-9, further comprising phase synchronization circuitry configured to synchronize a phase of the at least three AC signals with a phase of at least three AC signals in the dongle.

Example 11: The apparatus according to any one of examples 4-10, wherein the driver is configured to be connected to the location pad.

Example 12: The apparatus according to any one of examples 4-11, wherein the driver is built into to the location pad.

Example 13: A location pad driver apparatus, comprising: a connector configured to be physically connected to a location pad; wireless communication circuitry configured to wirelessly receive data about a current amplitude and a phase of at least three first alternating current (AC) signals generated at a patient interface unit (PIU) or a dongle connected to the PIU; and a signal generator configured to: generate at least three second AC signals responsively to the wirelessly received data about the current amplitude and phase; and provide the at least three second AC signals to at least three magnetic field generator coils disposed in the location pad in order to generate at least three corresponding alternating magnetic fields in a region around the location pad.

Example 14: The apparatus according to example 13, wherein the signal generator is configured to maintain the at least three second AC signals at the current amplitude of the at least three first AC signals.

Example 15: The apparatus according to any one of examples 13 and 14, further comprising: a clock configured to maintain a clock value and run at a clock frequency; and clock synchronization circuitry configured to synchronize at least one of the clock value or the clock frequency with a remote clock disposed in the dongle or the PIU.

Example 16: The apparatus according to any one of examples 13-15, further comprising phase synchronization circuitry configured to synchronize a phase of the at least three second AC signals with the phase of the at least three first AC signals.

Example 17: A catheter position tracking system, comprising: a patient interface unit (PIU) comprising: an interface configured to be connected to at least one catheter and a dongle which is configured to wirelessly connected to a location pad; and signal processing circuitry configured to process signals received from the at least one catheter; the dongle, which is configured to augment the PIU, the dongle comprising: a connector configured to be physically connected to the PIU; at least three load circuits configured to receive at least three corresponding first alternating (AC) signals from the PIU via the connector and mimic a load of at least three corresponding magnetic field generator coils of a location pad; sampling circuitry configured to sample a current amplitude and a phase of the at least three first AC signals in the at least three load circuits; and wireless communication circuitry configured to wirelessly send data about the current amplitude and the phase of the at least three first AC signals to the location pad; and the location pad comprising: a driver including wireless communication circuitry configured to wirelessly receive data about the current amplitude and the phase of the at least three first AC signals from the PIU; and a signal generator configured to generate at least three second alternating current (AC) signals having at least three corresponding different signal frequencies responsively to the data about the current amplitude and the phase of the at least three first AC signals; and at least three magnetic field generator coils disposed at different orientations to generate at least three corresponding alternating magnetic fields in a region around the location pad responsively to the at least three second alternating current signals being applied to the coils.

Various features of the disclosure which are, for clarity, described in the contexts of separate examples may also be provided in combination in a single example. Conversely, various features of the disclosure which are, for brevity, described in the context of a single example may also be provided separately or in any suitable sub-combination.

The examples described above are cited by way of example, and the present disclosure is not limited by what has been particularly shown and described hereinabove. Rather the scope of the disclosure includes both combinations and sub-combinations of the various features described hereinabove, as well as variations and modifications thereof which would occur to persons skilled in the art upon reading the foregoing description and which are not disclosed in the prior art.

What is claimed is:

1. A catheter position tracking system, comprising: a patient interface unit (PIU) comprising:
an interface configured to be connected to at least one catheter and a dongle which is configured to wirelessly connect to a location pad;
and signal processing circuitry configured to process signals received from the at least one catheter;
the dongle, which is configured to augment the PIU, the dongle comprising:
a connector configured to be physically connected to the PIU;
at least three load circuits configured to receive at least three corresponding first alternating current (AC) signals from the PIU via the connector and mimic a load of at least three corresponding magnetic field generator coils of a location pad;
sampling circuitry configured to sample a current amplitude and a phase of the at least three corresponding first AC signals in the at least three load circuits;
wireless communication circuitry configured to wirelessly send data about the current amplitude and the phase of the at least three corresponding first AC signals to the location pad;
and phase synchronization circuitry configured to synchronize a phase of signals generated in the at least three corresponding magnetic field generator coils with the phase of the at least three corresponding first AC signals in the at least three load circuits
and the location pad comprising:
a driver including wireless communication circuitry configured to wirelessly receive data about the current amplitude and the phase of the at least three corresponding first AC signals from the PIU;
and a signal generator configured to generate at least three second alternating current (AC) signals having at least three corresponding different signal frequencies responsively to the data about the current amplitude and the phase of the at least three corresponding first AC signals;
and at least three magnetic field generator coils disposed at different orientations to generate at least three corresponding alternating magnetic fields in a region around the location pad responsively to the at least three second AC signals being applied to the coils.

2. The catheter position tracking system according to claim 1, wherein the dongle further comprises:
a clock configured to maintain a clock value and run at a clock frequency; and
clock synchronization circuitry configured to synchronize a remote clock of the driver, which is configured to be connected to the location pad, with at least one of the clock value or the clock frequency.

3. The catheter position tracking system according to claim 1, wherein the location pad further comprises sampling circuitry configured to sample the current amplitude and phase of the at least three second AC signals, and wherein the wireless communication circuitry is configured to wirelessly send data about the current amplitude and the phase of the at least three second AC signals to the PIU.

4. The catheter position tracking system according to claim 3, wherein the signal generator is configured to maintain the current amplitude of the at least three second AC signals at the current amplitude of the at least three corresponding first AC signals.

5. The catheter position tracking system according to claim 3, wherein the signal generator is configured to adjust the current amplitudes of the at least three second AC signals in order to maintain the at least three second AC signals at the amplitude of the at least three corresponding first AC signals.

6. The catheter position tracking system according to claim 5, wherein the driver further includes:
a clock configured to maintain a clock value and run at a clock frequency; and
clock synchronization circuitry configured to synchronize at least one of the clock value or the clock frequency with a remote clock disposed in the dongle.

7. The catheter position tracking system according to claim 5, wherein the location pad further comprises phase synchronization circuitry configured to synchronize a phase of the at least three second AC signals with a phase of at least three corresponding first AC signals.

* * * * *